United States Patent
Zannoli

(10) Patent No.: US 10,874,784 B2
(45) Date of Patent: Dec. 29, 2020

(54) APPARATUS FOR CONTROLLING THE BIO-MECHANICAL VENTRICLE-AORTA MATCHING

(71) Applicant: Angiodroid S.R.L., San Lazzaro di Savena (IT)

(72) Inventor: Sebastiano Zannoli, Bologna (IT)

(73) Assignee: ANGIODROID S.R.L.

(*) Notice: Subject to any disclaimer, the term of this patent is extended or adjusted under 35 U.S.C. 154(b) by 95 days.

(21) Appl. No.: 15/747,593

(22) PCT Filed: Jul. 28, 2016

(86) PCT No.: PCT/IB2016/054516
§ 371 (c)(1),
(2) Date: Jan. 25, 2018

(87) PCT Pub. No.: WO2017/021830
PCT Pub. Date: Feb. 9, 2017

(65) Prior Publication Data
US 2018/0221552 A1 Aug. 9, 2018

(30) Foreign Application Priority Data
Jul. 31, 2015 (IT) .................. 102015000040802

(51) Int. Cl.
*A61M 1/10* (2006.01)
(52) U.S. Cl.
CPC ........... *A61M 1/1072* (2013.01); *A61M 1/106* (2013.01)
(58) Field of Classification Search
USPC .................................................... 600/17–18
See application file for complete search history.

(56) References Cited

U.S. PATENT DOCUMENTS

| | | | |
|---|---|---|---|
| 2003/0229263 A1* | 12/2003 | Connors | A61B 5/205 600/29 |
| 2008/0242921 A1* | 10/2008 | Dancu | G09B 23/28 600/36 |
| 2008/0294019 A1* | 11/2008 | Tran | A61B 5/0006 600/301 |

FOREIGN PATENT DOCUMENTS

| | | |
|---|---|---|
| WO | 9528974 | 11/1995 |
| WO | 0105446 | 1/2001 |
| WO | 2012071395 | 5/2012 |

OTHER PUBLICATIONS

International Search Report and Written Opinion of the International Searching Authority Application No. PCT/IB2016/054516 Completed: Sep. 13, 2016; dated Sep. 21, 2016 8 pages.

* cited by examiner

*Primary Examiner* — Nicole F Lavert
*Assistant Examiner* — Nicole F Johnson
(74) *Attorney, Agent, or Firm* — Ware, Fressola, Maguire & Barber LLP

(57) ABSTRACT

An apparatus for controlling pressure of a medical gas during treatment of a patient includes is a balloon (1) that through a catheter (2) is introducable into an arterial system of the patient, and a damping bag (20), of greater volume than that of the balloon (1), adapted to be loaded with medical gas at a compliance pressure (Pc) and placed in direct fluid communication with the balloon (1). The damping bag (20) is kept in direct fluid communication with the balloon (1) for the entire duration of the treatment of the patient. The apparatus further includes fine adjusting means (30) for acting on the damping container in such a way that the compliance pressure (Pc) is maintained between the systolic pressure and the diastolic pressure of the patient (Continued)

when the balloon is introduced into the arterial system of the patient and during the treatment of the patient.

9 Claims, 2 Drawing Sheets

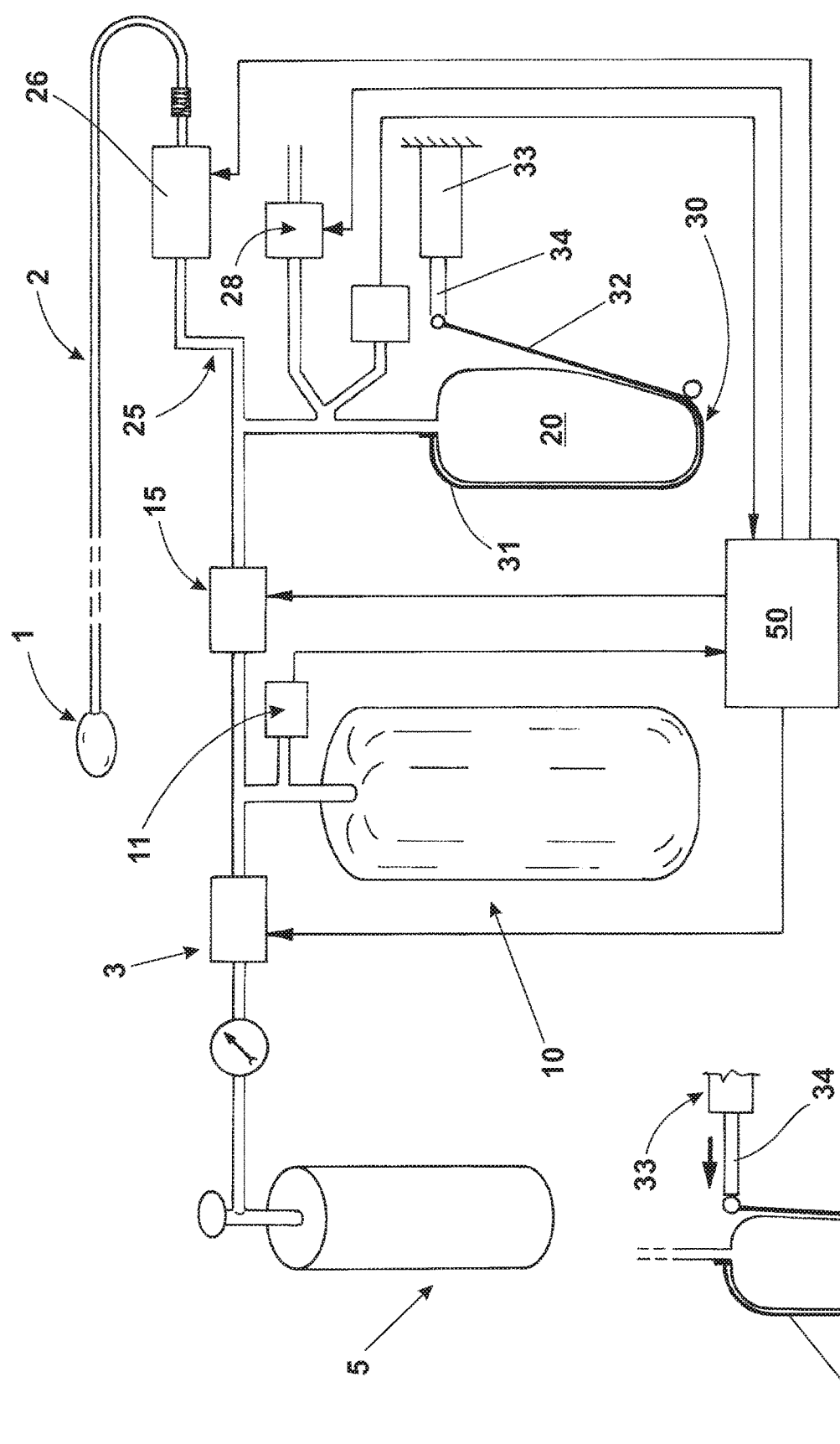
Fig. 1
Fig. 1a

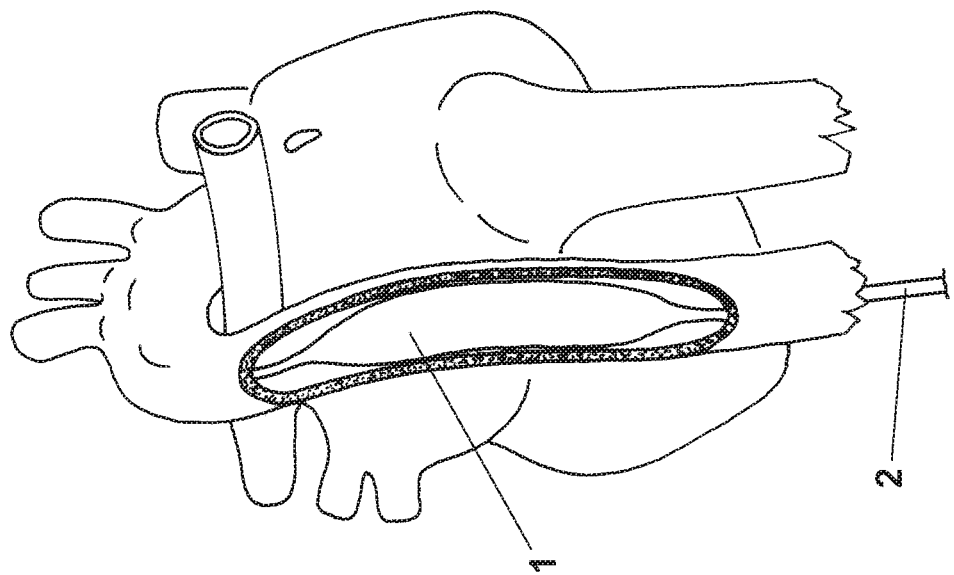
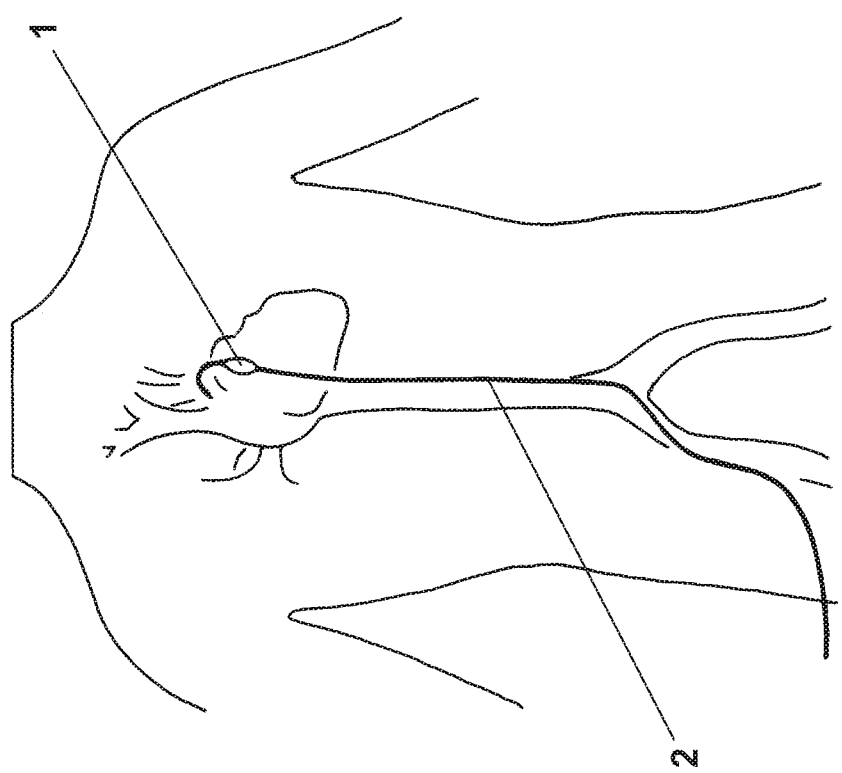

APPARATUS FOR CONTROLLING THE BIO-MECHANICAL VENTRICLE-AORTA MATCHING

BACKGROUND

1. Technical Field

The present invention relates to the field of medical devices for the treatment of diseases of the cardiovascular system. In particular, the invention relates to a device for maintaining the blood flow between the left ventricle and the aorta in conditions of alteration of the elastance of either system.

2. Discussion of Related Art

An adequate blood flow in large arteries from the heart (aorta and pulmonary artery) is produced by the periodic contraction of the ventricles, which provide the blood with the mechanical energy which is then dissipated at an arteriolar level. Since the ventricle and the artery are structures with elastic characteristics, the energy transfer between them depends on their mechanical adaptation in terms of instant elastance which can be altered, upward or downward, in many pathological conditions and significantly reduce the efficiency of the system. In practice, there may be two conditions: 1) a normal ventricle that fails to transfer its energy into an artery with increased elastance (atherosclerosis, hypertension, aortic dissection); 2) a ventricle with reduced elastance (heart failure, acute myocardial infarction, etc.) that fails to transfer its energy into a normal artery. Both cases result in a reduction of the blood flow and in the onset of a physiological deterioration condition which one attempts to counter with pharmacological aids or with mechanical support interventions.

The case of the left ventricle with functional limitations is what occurs more frequently in the clinical context and in order to solve this problem, the aortic counterpulsation technique has developed and widely spread, alongside—more recently and for a very limited number of cases and conditions—the implant of ventricular assistance devices (VAD).

The aortic counterpulsation is a technique, applied for over thirty years, which bases its effectiveness on the forced inflation and deflation of a balloon inserted into the aorta, in the descending section of the arch. Deflation occurs in the ventricular ejection step (systole) and promotes the transfer of blood into the aorta; inflation occurs in the ventricular filling step (diastole) when the aortic valve is closed, and promotes the shift of blood towards the periphery and coronary perfusion. This operating sequence must occur in a perfectly synchronized manner and is generally controlled by electrocardiogram. The balloon is placed into the aorta through a catheter inserted by femoral pathway and is inflated and deflated with helium gas. A modern counterpulsator includes: a balloon inflation pump, connected to the catheter inserted into the aorta; a cylinder containing medical grade helium, from which the gas to be supplied to the balloon is taken; a pump operation control device, which includes a patient's heart pulse detector and a computerized pump drive unit, as well as an interface for control by the operator.

The operation of this counterpulsator involves the withdrawal of a small amount of gas (usually 20-50 mL) from the cylinder, the periodic inflation and subsequent deflation of the balloon by means of the pump synchronously with the cardiac cycle detected from the patient.

The hemodynamic effects that counterpulsation aims to obtain consist of a drop in the systolic blood pressure and the resulting reduction of ventricular work, an increase in the diastolic blood pressure and resulting improvement of the coronary perfusion, a more or less marked increase in the cardiac output.

DISCLOSURE OF INVENTION

1. Technical Problem

In traditional aortic counterpulsation, due to the technical complexity and execution time of the pumping steps, it is not possible to manage the process quickly enough. For this reason, for each inflation cycle, the pump activation moment and thus of gas entry into the balloon, can only be of "predictive" type. This means that each command to activate the pump is based on the detection of the previous cardiac pulsation of the patient and not on the current one: all timing is calculated and controlled on the basis of the previous pulsation period. Since the constancy of the pulsation period of the patient is not always guaranteed, especially for patients in acute phase of circulatory shock, even the intervention of the counterpulsation device may not be perfectly in phase with the cardiac action, for a more or less consistent part of the working cycles. This can reduce, even substantially, the positive effect of the counterpulsation operations and bring a benefit not adequate to the patient's clinical needs.

The problem described exacerbates, up to cause not an advantageous condition but a clear disadvantageous condition, in the case of complex arrhythmias, unfortunately often associated with clinical conditions of use of the counterpulsator. Attempts to remedy these problems are increasingly efficient and technologically complex but this results in a continuous increase in the cost of apparatus and devices (e.g. balloon with fiber-optic catheter). Even with these limitations and operational complexity, the aortic counterpulsator remains the temporary mechanical support of choice in conditions of inadequate ventricular contractile function.

Both the aortic counterpulsation and the techniques that use implantable ventricular support devices aim to compensate the decrease of mechanical energy produced by the ventricle with an external source, either mechanical or electrical, without intervening directly on the mechanical mismatch between ventricle and aorta, which in many cases constitutes an important determinant of the critical situation. This choice has negative aspects that in some cases make the procedure inapplicable. This is the case in which the mechanical stress produced by the violent inflation of the balloon on the artery wall can result in a damage of the delicate biological structure (e.g. aortic dissection), whereby an intervention that would be necessary is not applied due to the risk to cause a damage greater than the probable advantage (the counter-pulsation in aortic dissection is contraindicated).

The apparatus currently used to carry out the counterpulsation, while being widely spread and considered to be indispensable in a modern therapeutic approach, have technological and operational complexity and high costs.

2. Objects of the Invention

The main object of the present invention is to provide an apparatus for promoting the transport of blood from the ventricle to the arterial system, and in particular to the aorta, through a direct intervention on the biomechanical matching features and, consequently, to improve the pumping efficiency of the ventricle.

Another object of the invention is to provide an apparatus that can adjust automatically and in a non-predictive manner to the variations in the heart rate of the patient treated.

A further object of the invention is to provide an apparatus able to ensure absolute and intrinsic safety of the intravascular mechanical stresses, preventing possible overpressure risks always present in active inflation systems.

Yet another object of the invention is to provide an apparatus of limited cost and complexity which can be used for different applications, even not provided for the traditional aortic counterpulsation.

3. Summary of the Invention

These and other objects are achieved by the apparatus for controlling the bio-mechanical ventricle-aorta matching of the present invention, implemented according to the present invention, intended to provide quantities of medical gas at a controlled pressure to a balloon, or other inflatable intra-aortic device, through a catheter introduced in the arterial system of the patient.

The apparatus includes: a damping bag, of greater volume than that of the balloon, adapted to be loaded with medical gas at a compliance pressure and placed in direct fluid communication with the balloon. The damping bag is kept in direct fluid communication with the balloon for the entire duration of the treatment of said patient.

In particular, the apparatus is for controlling the bio-mechanical ventricle-aorta matching of a patient, the apparatus including a balloon, or other inflatable intra-aortic device, through a catheter introduced in the arterial system of the patient, the apparatus being intended to provide quantities of medical gas at a controlled pressure to a balloon; a container that can be loaded with medical gas from a gas source, at a compliance pressure, and set in direct fluid communication with the balloon for the whole treatment of the patient, the apparatus being characterized in that the container consists of a damping container in the form of a bag, with the volume of the damping bag being significantly greater than the volume of the balloon, fine adjusting means of the compliance pressure being provided and acting on said dumping bag in such a way that the compliance pressure is maintained between the systolic pressure and the diastolic pressure of the patient.

The apparatus further includes: a maximum pressure reservoir that can be filled with medical gas at a maximum pressure to in turn fill the damping bag at the compliance pressure; compliance pressure detecting means in the damping bag; connecting means between the damping bag and the catheter, provided with operable compliance flow shutoff means; a control unit.

Further features and advantages of the apparatus are described below.

BRIEF DESCRIPTION OF THE DRAWINGS

The features of the invention that do not emerge from the above are highlighted in the following description, with reference to the accompanying drawing tables, in which:

FIG. 1 schematically shows the main components of the apparatus for controlling the mechanical ventricle-aorta matching and blood flow according to the invention;

FIG. 1a schematically shows a detailed view of the damping bag and of the mechanism for adjusting the pressure in the preferred embodiment of the invention.

FIG. 2 shows a view of a patient's trunk carrying a catheter with related balloon inserted in the descending section of the aortic arch;

FIG. 3 shows an enlarged detail of portion A in FIG. 2, which shows the heart muscle and said aorta portion with the inflated balloon in plain view.

DETAILED DESCRIPTION OF PREFERRED EMBODIMENTS OF THE INVENTION

With reference to said figures, there is shown an apparatus for controlling the mechanical matching and the aortic blood flow of a patient suffering from heart disease hospitalized in resuscitation or intensive care. In particular, the patient has a catheter 2 provided with a balloon 1 at the end, inflatable with a suitable gas, essentially of a known type. The gas used preferably but not exclusively consists of medical grade helium.

Balloon 1 is positioned at the beginning of the descending section of the patient's aorta, introducing catheter 2 into the vasculature, typically through the femoral artery, and has an internal gas pressure at an intermediate value between the maximum and minimum value present in the aorta. The function of balloon 1 is to reduce the ventricular load during the contraction and ejection of blood by a passive collapse, and withstand the aortic pressure during the diastolic phase by passive inflation. In its maximum inflation size, balloon 1 has such a section that it is not, at low flow rates, a significant reduction in the aortic lumen, so it is not a significant increase in the vascular resistance. During the treatment for controlling the mechanical ventricle-aorta matching and the blood flow, apparatus is placed in fluid communication with said balloon 1, through catheter 2, in a manner that will be explained in detail hereinafter.

The operations of apparatus are controlled by a control unit 50, including a suitably programmed computer and interface and connecting devices with an operator and with other devices in the apparatus itself, also in this case in a manner that will be better clarified hereinafter.

In essence, the basic structure of apparatus includes a maximum pressure reservoir 10, fillable with medical gas at a first predetermined pressure Pm. The filling of the maximum pressure reservoir 10 is made from a source 5 of such a gas, usually consisting of a cylinder loaded with the same and replaceable once exhausted.

Feeding flow shutoff means 3 are provided between cylinder 5 and the maximum pressure reservoir 10, connected to the control unit and operable by the same to flow an amount of medical gas sufficient to bring the pressure Pm therein to a predefined maximum value, such as 100 mmHg. The flow shutoff means 3 consist of a solenoid valve having suitable features, preferably of proportional type.

The apparatus continuously detects, through the catheter line and a dedicated external module (diagnostic unit monitoring system), the patient's arterial pressure, which is acquired by the control unit 50. The maximum and minimum arterial pressure can also be measured non-invasively and entered through the operator interface, making the instrument independent from any external acquisition system.

Maximum pressure detecting means 11, also connected to the control unit 50, are also provided in apparatus in fluid connection with the maximum pressure reservoir 10, to provide the same unit with information related to the pressure reached by the medical gas within the maximum pressure reservoir 10 itself.

Apparatus further comprises a damping container 20, preferably but not necessarily limp, for example consisting of a bag of gas-tight plastic material. Bag 20 is set in interruptible fluid communication with the maximum pressure reservoir 10 with the interposition of primary flow control and shutoff means 15 connected to the control unit 50 and operable by the same. The primary flow shutoff means 15 also consist of a solenoid valve having suitable features, preferably of proportional type or of a peristaltic or diaphragm pump.

In use, the damping bag 20 is filled with medical gas coming from the maximum pressure reservoir 10 up to a compliance pressure Pc set by the operator and comprised between the maximum and minimum arterial pressure of the patient.

Compliance pressure detecting means 21 are provided in apparatus, in fluid communication with the damping bag 20 and connected to the control unit 50 to provide the same with information on the current value of the same compliance pressure Pc.

The damping bag 20 is in turn set in fluid communication with balloon 1, through catheter 2, by connecting means 25, consisting of a conduit having appropriate structural and dimensional features to keep the pressure inside balloon 1 substantially identical to said compliance pressure Pc.

The volume of the damping bag 20 is conveniently greater than that of balloon 1 and it is indeed advisable, for the purposes of the invention, that the difference in volume is as high as possible.

Moreover, the volume of the maximum pressure reservoir 10 is also conveniently greater than the volume of the damping bag 20.

Output flow shutoff means 26 are provided between balloon 1 and the damping bag 20, also consisting of a solenoid valve, operable by the control unit 50 to interrupt the connection between said balloon 1 and reservoir 20 during the non-operational steps of the treatment.

Additional discharge flow shutoff means 28 are provided to set the damping bag 20 and the atmosphere in fluid communication, connected to the control unit 50 and operable by the same to empty reservoir 20 and balloon 1 into the atmosphere upon completion of the blood flow adjustment operations.

In its preferred but non-exclusive embodiment shown in FIGS. 1 and 1a, apparatus also comprises fine adjusting means 30 of the compliance pressure Pc, intended to act on the damping bag 20 to accurately define said pressure before or during the execution of the therapeutic step on the patient.

In particular, in the embodiment shown, the fine adjusting means 30 comprise a fixed structure 31, consisting of a rigid shaped plate, which surrounds the damping bag 20, and a movable structure 32, in turn consisting of a flat or also shaped plate. The movable structure 32 is hinged to one end of the fixed structure 31 and is operated, at the opposite end, by an actuator 33 by means of an operating stem 34.

Actuator 33 is conveniently of the type consisting of an electric stepper or brushless motor connected to the control unit (50) and operable thereby, able to accurately define the position of the operating stem 34, and thereby of the movable structure 32 with respect to the fixed structure 31.

Moving the movable structure 32 close to the fixed one 31 (FIG. 1a) by extending the operating stem 34 compresses the damping bag 20 and increases the internal pressure thereof. Moving the two structures apart decreases the pressure inside bag 20.

The operation of apparatus object of the invention is, in its essential steps, extremely simple.

Basically, once balloon 1 has been introduced at the descending section of the aortic arch and after the patient's arterial pressure has been detected through the catheter-balloon with independent external monitor or non-invasive technique, the maximum and minimum pressure values of the arterial pulse have been provided to the control unit 50, the latter actuates the supply valve 3 to open and the primary valve 11 to close to fill reservoir 10 with medical gas up to reaching the predefined maximum pressure, and in particular, preferably, the pressure of 100 mmHg.

Thereafter, the supply valve 3 is closed and the primary valve 11 is opened, with the outlet valve 26 in closed position, to fill the damping bag 20 until reaching a compliance pressure Pc whose value is determined by the operator as a function of the result to be achieved, but which is in any case comprised between the patient's maximum and minimum pressure.

The therapeutic step is preceded by a step of flushing and filling the balloon already inserted into the artery.

The conduit between the damping bag 20 and the atmosphere is first emptied and left filled with helium; then, balloon 1 is opened to the atmosphere, so that it collapses completely. Then, balloon 1 is filled through the line and is repeatedly emptied to the air. Finally, the collapsed balloon 1 is left connected to the line with the outlet valve 26 closed.

The primary valve 15 is then closed and the outlet valve 26 is opened to set the damping bag 20 in communication with catheter 2 and with balloon 1.

Consequently, the balloon expands until its internal pressure is in dynamic balance with the compliance pressure Pc pressure in the damping bag 20.

Upon the variation of the pressure in the aorta, the balloon will have a pulsing behaviour, inflating in the diastolic phase and collapsing in the systolic phase.

This dynamic behaviour, due to a continuous and bi-directional gas exchange between balloon and damping reservoir essentially produces the technical effect of the invention. In fact, balloon 1 is affected by various actions as a function of the cardiac cycle phases. During systole, the blood pressure in the aortic vessel increases to become greater than the compliance pressure Pc present in the damping bag 20 and into balloon 1, which thus collapses. During diastole, conversely, the blood pressure drops up to minimum values of the compliance pressure Pc and the balloon inflates. In the systolic phase, there is a flow of gas from the balloon to the damping bag 20, in the diastolic phase there is a flow of gas from the damping bag to the balloon. The effect is much more evident and clinically effective the greater the difference between the maximum and minimum pressure values and the pressure in the damping bag, and depends on the ratio of the volume of the same damping bag 20 to that of balloon 1.

The collapse and periodic inflation of the balloon results in a change of the bio-mechanical ventricle-aorta matching since the collapse during the blood ejection reduces the increase of the arterial pressure at equal volume variation (output), resulting in a decrease in the overall elastance of the arterial system (elastance=$\Delta P/\Delta V$). The ventricle, which has a reduced elastance due to the existing acute pathology, in the opening phase of the aortic valve, must therefore face a load with reduced and more appropriate elastance. In this respect, it should be noted that the optimum energy transfer condition is when the elastance of the two systems is similar. The dynamics of the balloon returns the arterial elastance to a value more similar to that, reduced, of the ventricle. The dynamic behaviour of the balloon changes by changing the internal pressure of the compensation chamber within the range between maximum and minimum pressure of the patient, therefore by changing this parameter it is possible, in the single patient, to adjust and optimize the bio-mechanical matching.

The advantages that are obtained from the bio-mechanical point of view consist in an improvement in the energy transfer efficiency from the heart muscle to the vascular system. In physiological terms, the benefit is twofold: 1) in the systolic emptying phase, the ventricle is facing a lower aortic pressure, and then generates a lower ventricular wall tension, a lower myocardial stress and a reduced oxygen consumption (very important element in a generator that is in very limited energy production conditions); 2) The increase of the diastolic arterial pressure, due to the inflation of the balloon, also causes an increase in the coronary flow and cerebral perfusion, elements that are not secondary in conditions of reduced cardiac output.

In practice, there is an improvement of the myocardial perfusion, a reduction of the myocardial oxygen consumption, an increase of the pump-load energy transfer efficiency. The best bio-mechanical matching not only improves energy transfer, in physiological terms it makes the generator (the ventricle) be able to produce the mechanical energy to a lower metabolic cost.

Apparatus may further include, programmed in the control unit 50, means for periodically detecting the variations in the compliance pressure Pc, however minimal, due to the difference in volume between balloon 1 and the damping bag 20, and associating such variations to the blood pressure in the artery and, as a function of these values, possibly setting the most suitable values for the compliance pressure Pc, introducing new medical gas in the damping bag 20 or releasing a part thereof to the atmosphere.

This operation can be alternatively carried out by monitoring the systemic pressure of the patient with external means connected, as said above, to the control unit 50, or in a non-invasive manner with arterial occlusion technique.

A further advantage ensured by the apparatus object of the invention is the fact that since the bio-mechanical matching effect is totally passive, it takes place in perfect synchronization with the patient's cardiac cycle, even if this is not of constant duration or if there are arrhythmias.

Moreover, the treatment is carried out in absolute safety, since any adjustment operations of the compliance pressure Pc are carried out by withdrawing medical gas from the maximum pressure reservoir 10, whose maximum pressure Pc is still not greater than the patient's systolic pressure, and not directly from cylinder 5, in which the gas is contained at much greater and potentially dangerous pressures.

Moreover, apparatus has a simple structure and can be implemented in a particularly cost-effective manner.

It is understood that the described apparatus can be used, making appropriate variations which still fall within the subject inventive concept, also in other areas and sectors, without departing from the spirit of the invention.

It is also understood that different embodiments or variants of the present apparatus fall within the protection scope of the present invention as described above and defined in the following claims.

The invention claimed is:

1. An apparatus for controlling pressure of a medical gas during treatment of a patient, said apparatus comprising:

a balloon (1), or other intra-aortic device inflatable to a volume, that through a catheter (2) is introducable into an arterial system of the patient, the apparatus providing quantities of the medical gas at a controlled pressure to the balloon when introduced into the arterial system of the patient and during the treatment of the patient;

a container (20) that is loadable with the medical gas from a medical gas source (5), at a compliance pressure (Pc), and set in direct fluid communication with the balloon (1) for the treatment of the patient when the balloon is introduced into the arterial system of the patient, wherein the container consists of a damping container (20) having the form of a damping bag, with the volume of the damping bag comprising a volume significantly greater than the volume of the balloon (1) when provided with the quantities of medical gas at the controlled pressure; and fine adjusting means (30) for acting on the damping container such that said compliance pressure (Pc) is maintained between a systolic pressure and a diastolic pressure of the patient when the balloon is introduced into the arterial system of the patient and during the treatment of the patient, wherein said compliance pressure (Pc) is not less than the diastolic pressure of the patient;

a maximum pressure reservoir (10) that is filllable with said medical gas from the source (5) of said medical gas at a predetermined maximum pressure (Pm), wherein said damping bag (20) is set in interruptible fluid communication with said maximum pressure reservoir (10) and fillable with said medical gas from the pressure reservoir at said predetermined compliance pressure (Pc) that is not greater than said maximum pressure (Pm);

first operable flow shutoff means (15) for the interruption of flow, interposed between said maximum pressure reservoir (10) and said damping bag (20), fit to allow or interrupt on command the flow of said medical gas therebetween;

compliance pressure detecting means (21), arranged in fluid communication with said damping bag (20), for detecting the pressure of the medical gas inside the damping bag:

connecting means (25) between said damping bag and the catheter (2), provided with second operable output flow shutoff means (26); and a control unit (50) connected to said first operable flow shutoff means (15), to said compliance pressure detecting means (21) and to said operable compliance flow shutoff means (26) for adjusting pressure within the damping bag (20) in order to control blood flow as a function of a difference between the gas pressure within the damping bag and, consequently, inside the balloon (1), and blood pressure generated by a pulse of a ventricle of the patient;

wherein said control unit (50) is responsive to a detected compliance pressure (Pc) signal from said compliance pressure detecting means (21) for operating said first (15) and second (26) flow shutoff means in order to change said compliance pressure (Pc) within the damping bag (20) as a function of detected variations of said compliance pressure (Pc).

2. The apparatus according to claim 1, wherein said compliance flow shutoff means (26) comprise a normally open solenoid valve, and are kept in open position for substantially an entire duration of the treatment of the patient, to maintain said balloon (1) and said damping bag (20) in direct fluid communication.

3. The apparatus according to claim 1, wherein said maximum pressure (Pm) for loading said maximum pressure reservoir (10) substantially coincides with the systolic pressure of the patient.

4. The apparatus according to claim 1, further comprising maximum pressure detecting means (11) set in fluid communication with said maximum pressure reservoir (10) for detecting an internal pressure of the medical gas therein, the detecting means connected to the control unit (50) so that information related to said pressure pulse and to a gas exchange between said balloon (2) and dumping bag (20) is sent from the maximum pressure detecting means (11) to the control unit.

5. The apparatus according claim 1, further comprising operable feeding flow shutoff means (3), which are interposed between the medical gas source (5) and the maximum pressure reservoir (10), the feeding flow shutoff means connected to the control unit (50) and controlled by the control unit in order to load said maximum pressure reservoir (10) with the medical gas from the medical gas source (5).

6. The apparatus according to claim 1, further comprising discharge flow shutoff means (28) set in fluid communication with said damping bag (20) and with the atmosphere, connected to said control unit (50) and controlled by the control unit to discharge the medical gas contained in said damping bag (20) and balloon (1) to the atmosphere.

7. The apparatus according to claim 1, wherein said fine adjusting means (30) is for adjusting said compliance pressure (Pc), by acting on said damping bag (20).

8. The apparatus according to claim 7, wherein said fine adjusting means (30) comprises a fixed structure (31) that envelops said damping bag (20) on at least one side thereof, and a movable structure (32), hinged to an end of said fixed structure (31) and operated at the opposite end by an actuator (33) by means of an operating stem (34), said actuator connected to and operated by said control unit (50).

9. The apparatus according to claim 8, wherein said actuator (33) consists of a stepper or brushless motor.

* * * * *